United States Patent [19]

Ewing

[11] Patent Number: 4,478,225
[45] Date of Patent: Oct. 23, 1984

[54] HEART MONITOR FOR HORSES

[76] Inventor: John G. Ewing, 1515 Glenmere Rd., Greeley, Colo. 80631

[21] Appl. No.: 446,321

[22] Filed: Dec. 2, 1982

[51] Int. Cl.³ .............................................. A61B 5/04
[52] U.S. Cl. ............................. 128/706; 128/644
[58] Field of Search ............... 128/639, 643, 644, 690, 128/696, 706

[56] References Cited

U.S. PATENT DOCUMENTS

| | | | |
|---|---|---|---|
| 3,530,851 | 9/1970 | Geschickter | 128/644 |
| 3,595,218 | 7/1971 | Kirkpatrick et al. | 128/643 |
| 3,702,113 | 11/1972 | Blockley | 128/639 |
| 3,848,582 | 11/1974 | Milani et al. | 128/639 |
| 4,114,352 | 9/1978 | Horton et al. | 128/639 |
| 4,202,350 | 5/1980 | Walton | 128/690 |
| 4,221,223 | 9/1980 | Lindon | 128/706 |
| 4,278,095 | 7/1981 | Lapeyre | 128/707 |
| 4,319,581 | 3/1982 | Cutter | 128/707 |

Primary Examiner—William E. Kamm
Attorney, Agent, or Firm—William P. O'Meara

[57] ABSTRACT

A heart rate monitor for measuring the heart rate of a horse which is effective during training as well as other periods is disclosed. The heart rate monitor comprises electrode means mounted in the girth of a saddle for detecting heart related electrical signals on the surface of the horse's body. The heart monitor also comprises signal processing circuitry means and display means which may be enclosed in a housing and are mounted on the horse's saddle and easily readable by a person sitting in the saddle. Shielded electrical connection means for transmitting an electrical signal from the electrodes to the signal processing circuitry means are also disclosed.

20 Claims, 8 Drawing Figures

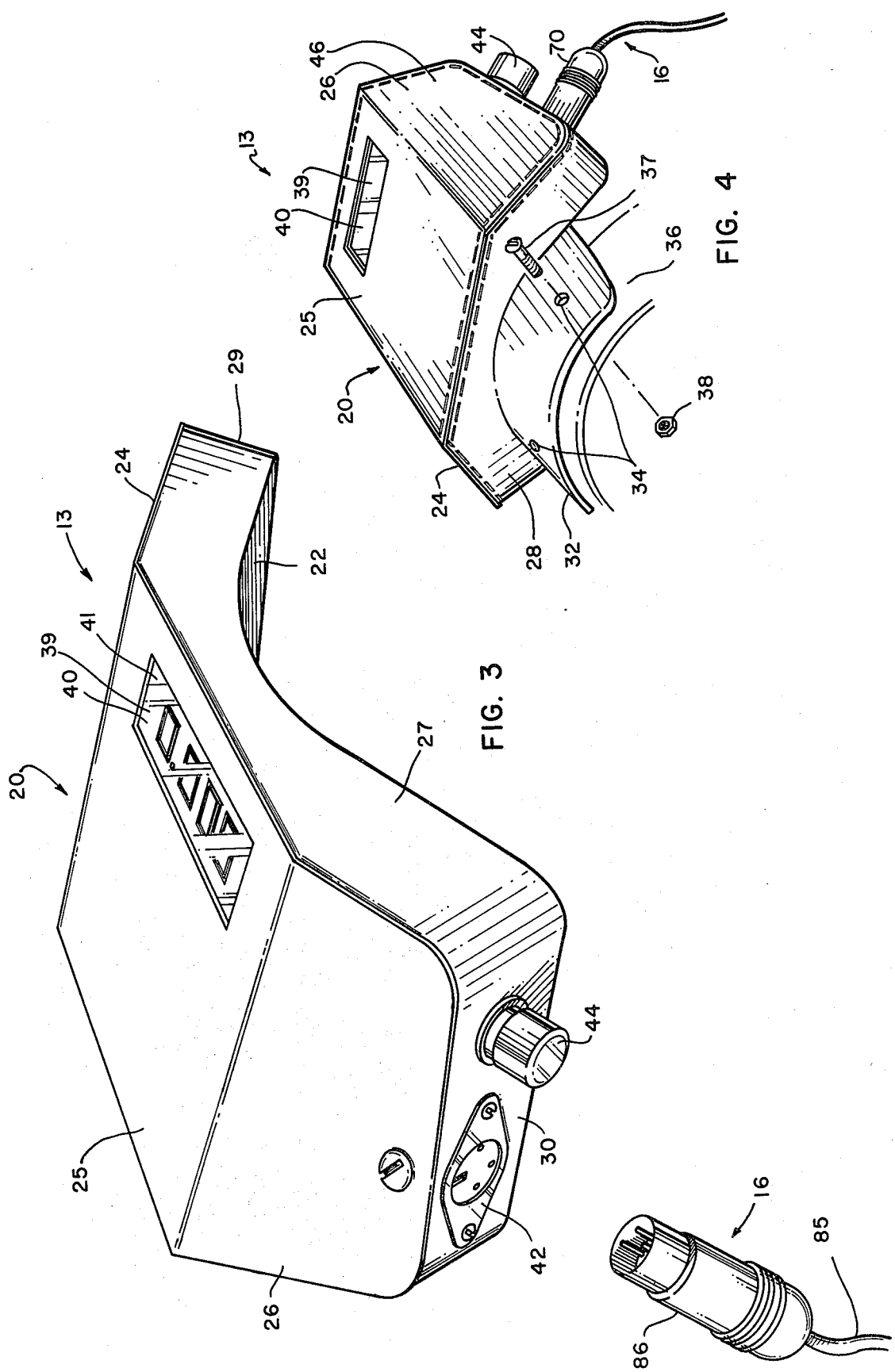

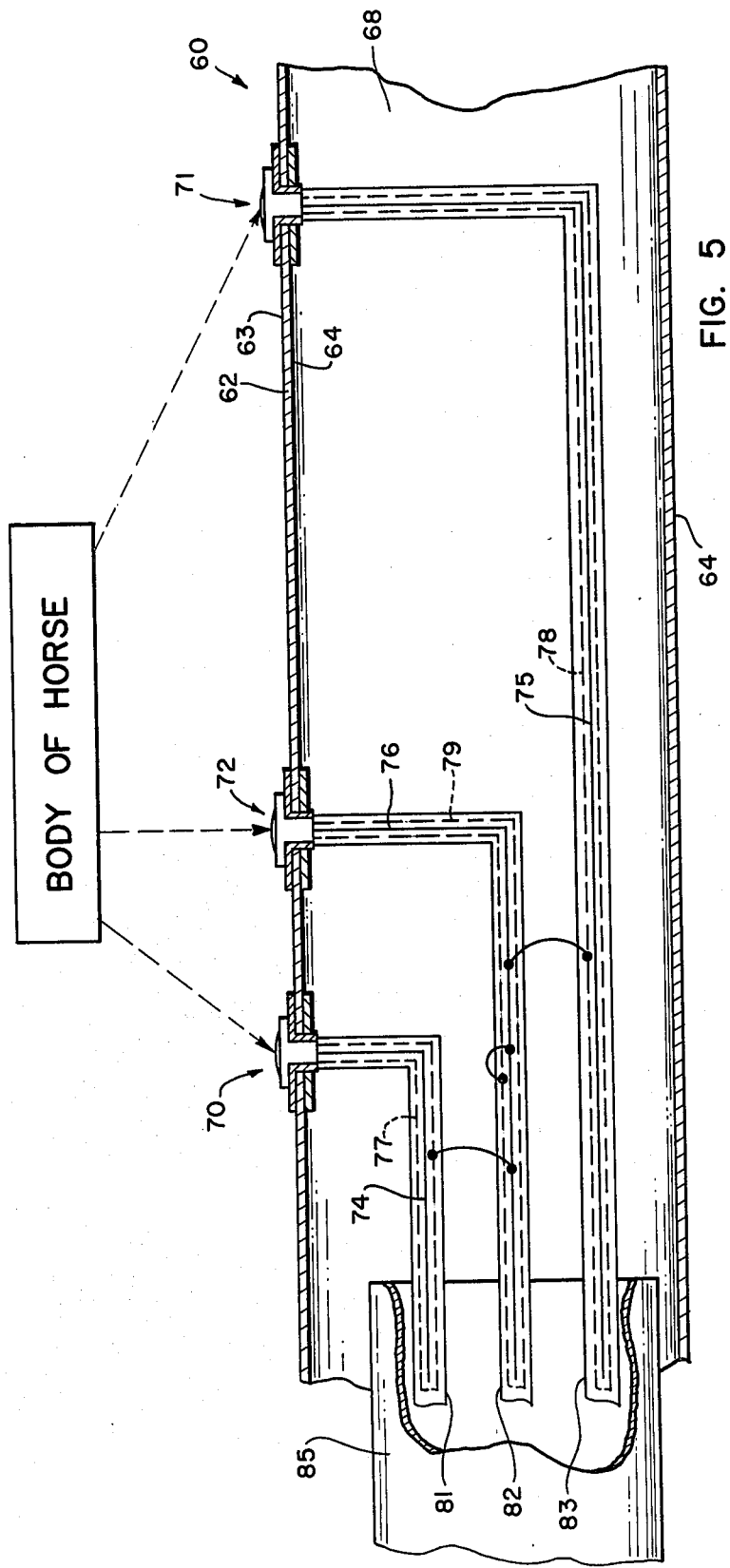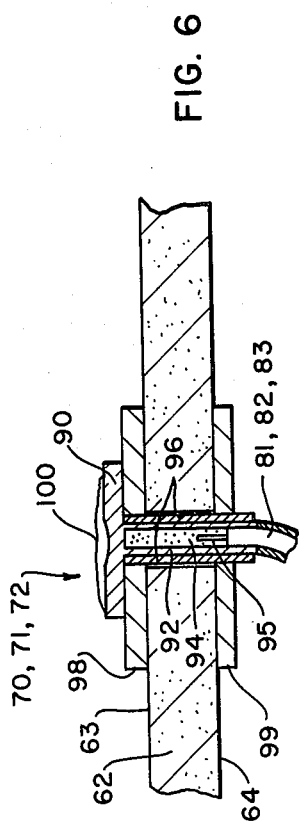

HEART MONITOR FOR HORSES

The present invention relates generally to medical and training devices for horses and more specifically to a heart rate monitor which may be used to monitor the heart beat of a horse during training.

A number of devices are presently available for the monitoring of heart beats of a human patient. Such devices have long been in use in hospitals for the purpose of monitoring a patient's heart beat during operations or to monitor vital signs in critically ill patients, etc. Heflin U.S. Pat. No. 3,638,642 discloses one such device.

In recent years compact electronic components have made it possible to provide human heart rate monitors which are generally portable. Some units of this type sense the heart beat by means of a transducer which physically senses the heart beat and provides an electric signal in response thereto which is processed to provide pertinent information such as heart beats per minute, etc. Orr et al., U.S. Pat. No. 3,807,388, Geneen, U.S. Pat. No. 3,978,849 and Wade, U.S. Pat. No. 3,572,322 discloses heart rate monitors of this type. Other heart rate monitors sense voltage fluctuations at the surface of a person's skin through the use of external electrodes. Certain voltage fluctuations on a person's skin surface correspond to the person's heart pulse. Suitable filtering means may be provided in electronic circuitry for filtering out electronic signals not related to the heart beat and the heart related signal may be amplified and processed by the circuitry to provide output relating to the heart rate such as visual display of heart beats per minute, audible danger signals at predetermined heart rate levels, etc. Huber, U.S. Pat. No. 3,863,626 discloses apparatus for surveying and indicating the physical efforts of an individual which is adapted to produce a signal when the pulse rate reaches a limit value. Huber also discloses electrodes mounted in a belt attached about the individual's chest. Cutter, U.S. Pat. No. 4,319,581 discloses a heart pulse monitor apparatus having electrodes mounted in the handle portions of a bicycle with a pulse monitoring apparatus provided on one of the hand grips.

Although numerous heart monitors have been provided for use by humans, there has been, until the present invention, no heart rate monitor which may be used effectively with a horse during training periods.

During the training of horses, generally, and especially during conditioning training for thoroughbred race horses, it is desirable to push the animal beyond its present degree of conditioning for short periods in order to improve the animal's level of conditioning. However, if the animal is stressed beyond its conditioning level for an extended period of time, the likely effect is to exhaust the animal and hamper its performance in the near future. The stress level during work outs is extremely important for race horses since it is desireable to train an animal to its maximum level of conditioning prior to a race without overtraining it and hampering its race performance. Presently race horse training is a very intuitive art which requires years of experience on the part of trainers and jockeys to sense the proper levels of training for various horses since each horse generally responds differently to training and has individual stress and conditioning characteristics. With the present invention, the horse's heart rate may be accurately monitored and observed during training, allowing the jockey to know how much the horse is being stressed by the exercise from the degree of increase in the heart rate. The invention thus eliminates much of the uncertainty from horse training and conditioning.

Such a device to be effective, must provide an easily read display which a rider may read at a glance while the horse is actively training. The device must be capable of detecting the horse's pulse rate in spite of the thick layer of hair covering the horse's body and should be easily transferable from horse to horse, requiring no surgical implants or special treatment, of the horse's body.

SUMMARY OF THE INVENTION

The present invention comprises a horse heart rate monitoring device having girth mounted electrode means which detect voltage fluctuations at the surface of the horse's body. Three electrodes are provided on the surface of the girth which contacts the body of the horse. The electrodes may be coated with electrically conductive salve or the like to improve electrical contact with the horse. An electronic circuit means and display means are provided in a housing mounted on a forward portion of a saddle which is firmly secured to the horse by means of the girth. The electrode means is placed in electrical connection with the circuit means by an electrical connection means comprising shielded wire leads running from each of the electrodes. The electrical connection means is adapted to mate with a socket in the circuit and display housing. A fluctuating voltage signal associated with the horse's heart beat is picked up by the electrodes and transmitted through the connection means to the circuit means where it is filtered to remove other electrical signals and processed to provide a human readable display of the horse's heart rate. In one preferred embodiment, the display comprises a liquid crystal display (LCD).

Accordingly, it is among the objects of the present invention to provide a heart rate monitor for horses.

It is another object of the invention to provide a heart rate monitor which may be used on horses during training and other periods of motion.

It is a further object of the invention to provide a heart rate monitor for horses which may be read by the trainer or jockey seated on the animal being trained.

It is a further object of the invention to provide a heart rate monitor for horses having girth mounted electrodes and a saddle mounted housing for electrical circuitry and a human readable display.

It is a further object of the invention to provide a heart rate monitor for horses wherein the housing for mounting the circuitry and the display is disconnectable from the girth mounted electrodes whereby the girth may be disconnected from the saddle and whereby interchangable girths may be used to make the saddle adaptable for a number of horses of different size.

It is a further object of the invention to provide a heart rate monitor for horses having a leather covered housing.

It is a further object of the invention to provide a heart rate monitor for horses wherein the electronic circuitry limits the rate of change of the human readable display.

It is a further object of the invention to provide a heart rate monitor for horses which is of sturdy construction and extemely safe in operation for both horse and rider.

BRIEF DESCRIPTION OF THE DRAWING

An illustrative and presently preferred embodiment of the invention is shown in the accompanying drawing in which:

FIG. 3 is a perspective view of a housing for a horse heart rate monitor circuit and display.

FIG. 4 is a perspective view of the horse heart rate monitor housing of FIG. 3 illustrating attachment thereof to the pommel of a saddle.

FIG. 5 is a schematic cut-away drawing of a portion of a girth illustrating the placement and attachment of electrodes and electrical connection means of a horse heart rate monitor.

FIG. 6 is a detailed view of an electrode of FIG. 5 illustrating the mounting thereof in the girth.

DETAILED DESCRIPTION OF THE INVENTION

Figure 1:
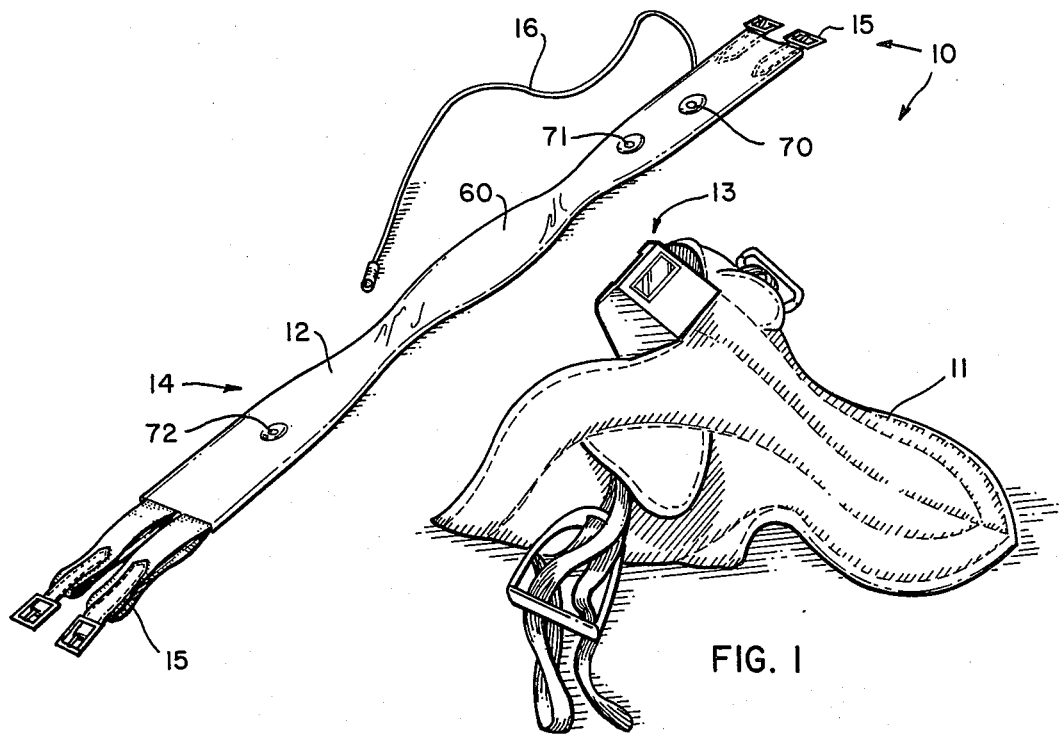
FIG. 1 is a perspective view of a horse heart rate monitor mounted on a saddle and girth.
Figure 2:
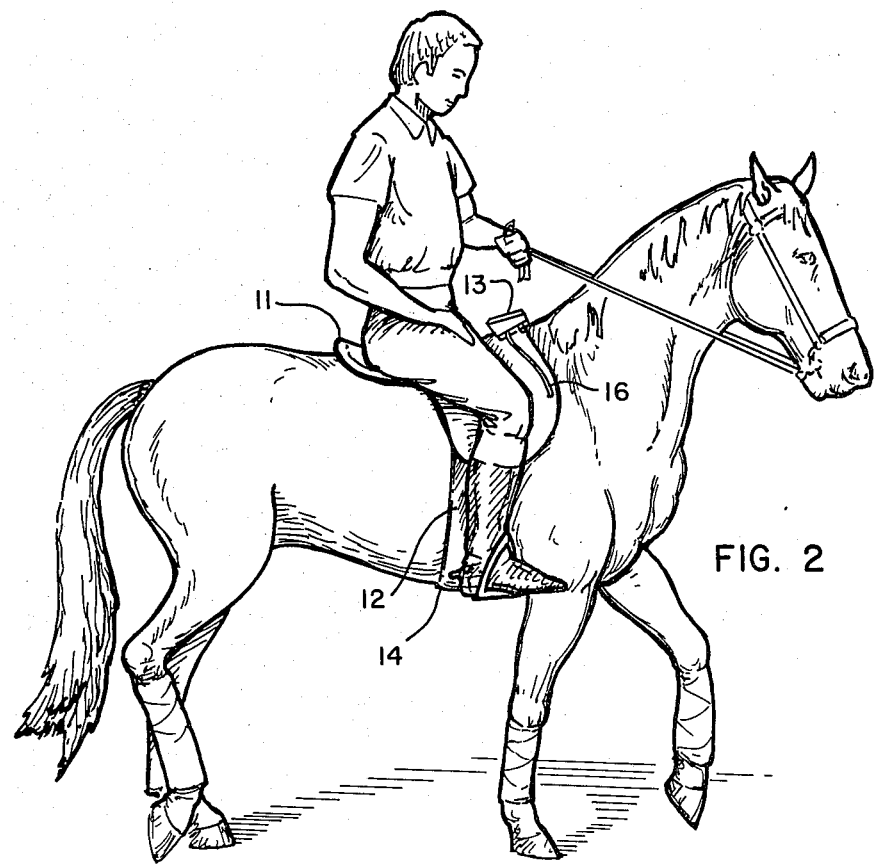
FIG. 2 is a perspective view of a saddle and girth mounted horse heart rate monitor being used on a horse during training.

As illustrated by FIG. 1, the heart rate monitor 10 of the present invention is mountable on a saddle means such as conventional saddle 11 and a girth means such as conventional girth 12, which may be removably attachable to saddle 11 by attachment means such as buckles 15 or the like. The heart rate monitor 10 comprises a saddle mounted circuit and display means 13 and a girth mounted electrode means 14 which is removably electrically connectable to the electrode means 14 by an electrical connection means 16. The electrode means may comprise three spaced apart electrodes 70, 71, 72 which come into contact with the horse's body when the girth and saddle are mounted on the horse as illustrated in FIG. 2. The electrodes provide an electrical signal which is dependent on the horse's heart rate to electrical circuit means 110, FIGS. 7 and 8, which causes a visual display 40 on the circuit and display means 13 to display the horse's heart rate in conventional units, such as beats per minute. The apparatus thus allows a rider, seated in the saddle 11, to observe the horse's heart rate at any time during training.

Referring to FIGS. 3 and 4, it may be seen that the saddle mounted circuit display means 13 comprises a housing means which in the presently preferred embodiment comprises a closed metallic box housing 20. The housing 20 has a curvilinear lower surface 22 having a radius of curviture approximating that of a saddle pommel portion 36. The housing of the preferred embodiment also comprises a flat top mid surface 25, and downwardly inclined top left and right hand surfaces 24, 26. The top surfaces 24, 25, 26 are joined with the lower surface 22 by forward, rear, left, and right lateral edge surfaces 27, 28, 29, and 30 which are oriented generally perpendicularly to said top and lower surfaces. A curvilinear attachment plate 32, having a radius of curvature substantially equal to the radius of curvature of the lower surface 22 and the saddle pommel 36, may be welded or otherwise rigidly attached to the housing lower surface 22. The plate 32 projects rearwardly from the housing 20 and is positionable in abutting circumjacent relationship with the pommel 36 and attachable thereto by suitable attachment means such as nuts and bolts 37, 38 and a plurality of holes 34 provided in the plate 32 and pommel 36 for accepting the bolts 38. The top mid surface 25 of the housing 20 is provided with a cut out portion 39 to allow viewing of a display means such as a liquid crystal display (LCD) 40 operably mounted within the housing. Cut-out portion 39 may be provided with a sealed transparent member 41 such as glass or plastic to prevent entry of foreign matter into the housing. A socket means is provided on the housing for attachment of the electrical connection means 16 thereto. In the presently preferred embodiment, the socket means comprises a female socket 42 provided on the right lateral edge surface 30 of the housing 20. A switch tripping means such as on-off push button 44 may also be provided on the housing and in the presently preferred embodiment is provided on the lower right edge surface 30. Thus a person riding a horse may conveniently switch the unit on or off. As illustrated by the dashed lines of FIG. 4, the housing 20 may be provided with a leather cover 46 similar in color and texture to that of the saddle in order to provide an aesthetically pleasing appearance when the housing 20 is mounted on the saddle 11.

As illustrated by FIGS. 1 and 5, the girth means 14 comprises an elongate body portion 60 which is preferrably constructed of leather. The leather may be folded and stitched together to form a flat member having an elongate cavity 68 therein defined by girth body upper portion 62, lower portion 66, and edge portions connecting the upper and lower portions. As shown by FIG. 5 the girth upper portion 62 in turn comprises an upper portion, upper surface 63 and upper portion, lower surface 64. The three spaced apart electrodes 70, 71, 72 are mounted in the girth body upper portion 62 in a manner to prevent electrical contact as described in further detail below. The two outboard most electrodes 70, 71 are active electrodes and the inwardly positioned electrode 72 is an indifferent electrode. The electrodes 70, 71, 72 are used in a conventional manner well known in the arts to sense voltage changes on the skin surface of the horse for generating an electrocardiogram (ECG) electrical signal which is processed as described in further detail below to generate a display of the heart rate of the horse. Each electrode 70, 71, 72 is electrically connected to an electrode wire 74, 75, 76 as described below for transferring an electrical signal to signal processing control circuitry 110. Each electrode wire 74, 75, 76 is coated with a non-conductive substance such as rubber, plastic or the like (not shown). Each wire 74, 75, 76 is also encompassed by an electrode wire shield 77, 78, 79 which shields the wires from electrical noise that might otherwise interfere with the electrical signal passing from the electrodes 70, 71, 72 to the signal processing circuit means 110. As illustrated by FIG. 5, each of the electrode wire shields 77, 78, 79 is grounded to the indifferent electrode wire 76. The shields 77, 78, 79 may be constructed of tinned copper or other suitable shielding material.

Each electrode wire shield 77, 78, 79 may in turn be encased in an encompassing electrically non-conductive casing 81, 82, 83 and all three of the electrode wires, thus encased, are in turn collectively encased in a nonconductive abrasive resistant exterior casing 85, which extends from the interior girth cavity 68 to a male adapter 86 or other plug means for attaching the electrical connection means 16 to the socket 42 in housing 20. Such three strand shielded electrode wire suitably encased in a protective casing is commercially available, such as Part No. YR-15593, manufactured by Graphic Controls Canada, Ltd. of Gananoque, Ontario, Canada. In the presently preferred embodiment the male adapter 86 has a three prong plug corresponding to the three electrode wires 70, 71, 72 which place the electrodes in signal transmitting electrical contact with the signal processing circuitry means 110 as described in further detail below.

The connection of the electrodes 70, 71, 72 to the girth upper portion 62 and the connection of the electrode wires 74, 75, 76 to the electrodes 70, 71, 72 is illustrated in FIG. 6. Each electrode comprises a generally tack shaped three dimensional object having a T-shaped cross section comprising a solid branch portion 90 and a hollow trunk portion 92. The terminal end 95 of an electrode wire 74, 75, 76 may be inserted into the hollow trunk portion 92 and securely retained therein in electrical contact with the branch portion 90 by means of solder or the like. The electrode is isolated from lateral edge surfaces of an electrode accepting hole in upper portion 62 by means of a sleeve 96 made from non-conductive plastic material or the like which is securely fitted about the trunk portion 92. The electrode is further isolated from the upper and lower surfaces 63, 64 of the girth upper portion 62 by means of non-conductive washers 98, 99 which may be made from mylar, neoprene or the like. The upper branch portion 90 of the electrode may contain a concave portion 97 therein for receiving a salve 100 or the like to insure proper electrical contact between the electrode and the body of the horse.

The signal processing circuitry means 110 will now be described with reference to FIGS. 7 and 8.

The use of the electrodes placed on the surface of the skin to generate an electrical signal having fluctuations therein corresponding to the heart beat of the electrode wearer is well known in the art. The expansion and contraction of the heart muscle during a heart beat produces a change in electrical voltage on the surface of the skin which varies from point to point on the body. These voltage fluctuations when monitored display various repeating wave forms including wave forms known are an R-wave and an S-wave. By using suitable filtering and signal conditioning techniques, the portion of the surface voltage signal created by such heart related wave forms may be separated from other signals caused by other muscle potentials. In the preferred embodiment, a signal filter tuned to a frequency of approximately 17 Hz is used to eliminate muscle potentials other than those produced by the heart of the horse. This filter may be provided within an amplifier 120, as illustrated in FIG. 7, or may be provided in a separate filter component 152, as illustrated in FIG. 8.

Figure 7:
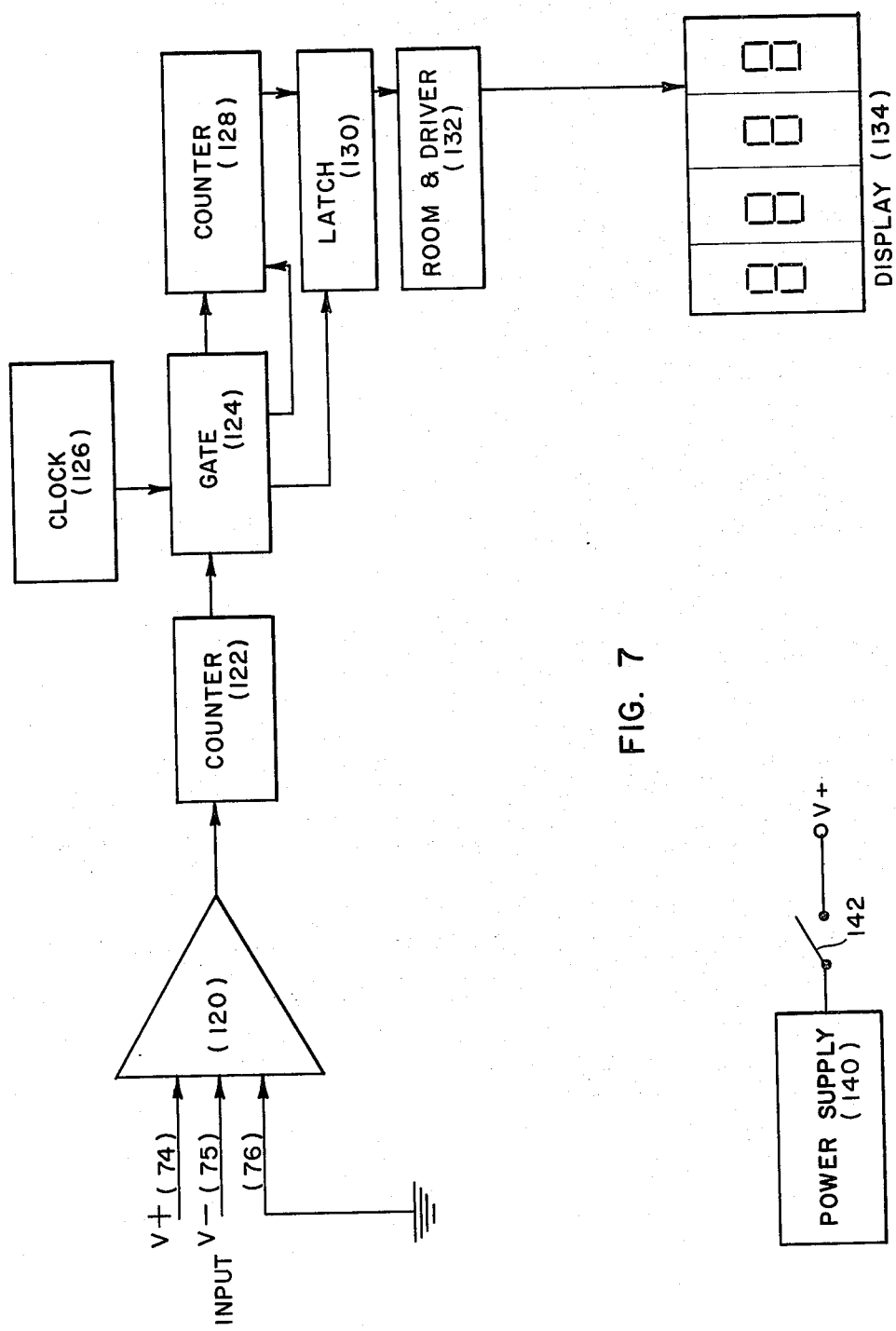
FIG. 7 is a schematic drawing illustrating the circuit components of a signal processing circuit means for a horse heart rate monitor.

In the signal processing circuitry means illustrated by FIG. 7, the electrode wire leads 74, 75, 76 are conventionally attached to an amplifier 120. R-waves generated by the horse's body are picked up by the electrode 70, 71, 72 and transmitted to the amplifier 120 where they are filtered and amplified by conventional means well known in the art. The amplifier 120 generates an electric pulse corresponding to each detected R-wave pulse and the signal thus generated is input to a counter 122 of conventional construction which in turn generates an output signal each time a predetermined number of R-wave pulses are counted. Each output of counter 122 actuates gate 124 to reset counter 128 and to input a stream of clock pulses from clock 126 into counter 128 during the period between successive gate actuations. Gate 124 also actuates a latch 130 at the end of each said predetermined number of R-wave pulses so as to store the last count contained in counter 128. The data stored in latch 130 is then input into the ROM and indicator driver unit 132, which converts each input of the counter 128 into a signal suitable for causing display indicator 124 to display a number indicative of the average heart pulse rate which occured during the count period determined by counter 128.

Although it would be possible to display the heart rate as determined between each consecutive R-wave pulse, this would not be practical because it is well known that the intervals between successive heart pulses fluctuate materially and consequently provide little useful information. A much more meaningful measure of pulse rate is attained by averaging. The first counter 122 counts the pulses output from amplifier 122 and upon the count of a predetermined number of heart pulses, such as for example 10, causes counter 128 to count clock pulses continuously over each 10 R-wave pulsations before the result is stored in latch 130. ROM 132 is thus programmed to convert the count contained in latch 130 into a digital output corresponding to the average clock count over the 10 pulsations and such output will cause a number to be displayed by unit 134 which represents the horse's pulse rate. Also contained within the housing 20 is a suitable power supply 140 such a nine volt alkaline battery for providing operative power to the various components of the circuit and display. A simple manual switch 142, which may be actuated by an exterior on-off switch means 44, FIG. 3, is provided for turning the circuit 110 on and off. In operation, once the switch 142 is closed, the device will be ready to count the R-wave pulses of the horse.

It will be readily understood by those skilled in the art, that the R-wave voltages generated by the horse's body will be applied across the input terminals of the amplifier 120, causing it to generate a series of R-wave pulses which will be counted by counter 122 and used to actuate gate 124 and input pulses from the one Kz clock 126 into counter 128. Counter 128 will then continue to count during the next 10 R-wave pulses at the conclusion of which the count in counter 128 will be output to latch 130 and counter 128 will be reset to begin another count sequence. Latch 130 will then input its contents to ROM and driver unit 132 which will in turn output signals for driving the digital display 134.

Figure 8:
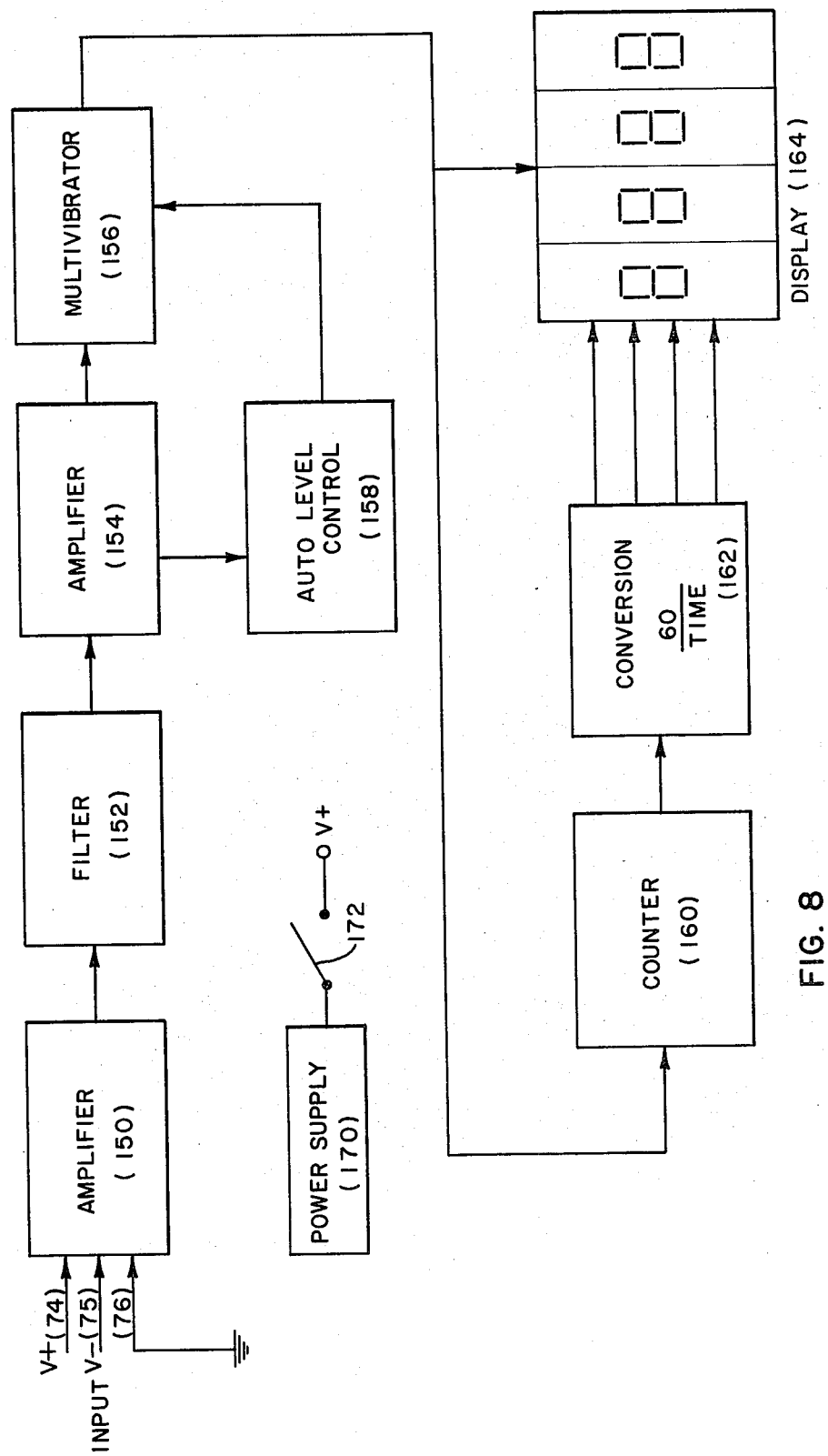
FIG. 8 is a schematic illustration of an alternate embodiment of components of a signal processing circuit means for a horse heart rate monitor.

An alternate embodiment of the invention is illustrated in FIG. 8 in which the horse's electrocardiagraphic signal is transmitted to amplifier 150 through leads 74, 75, 76. The incoming signal is amplified by differential amplifier 150 and fed into a narrow band filter 152 to reduce muscle artifact. Filter 152 is tuned to 17 Hz. The signal is then further amplified and conditioned by amplifier 154, then used to trigger a mono-stable multivibrator 156 which produces a high frequency digital pulse. The triggering level of the multivibrator 156 is automatically adjusted by an autolevel control unit 158. The multivibrator 156 pulse is fed to a digital counting circuit 160, counting circuit 160 counts the time interval between each succeeding pulse. A beat per minute count is then arrived at by a conversion circuit 162. The result is then fed to the display unit 164 comprising liquid crystal displays. A heart beat per minute indication on the display is achieved by triggering with the multivibrator 156 pulse. The circuit means 110 may use CMOS logic and LCD displays to reduce power consumption from power supply means 170. Power supply means 170 is provided with an on-off switch 172 to turn the unit on and off.

It is contemplated that the inventive concepts herein described may be variously otherwise embodied and it is intended that the appended claims be construed to include alternative embodiments of the invention except insofar as limited by the prior art.

What is claimed is:

1. A heart monitor for measuring the heart rate of a horse during training and other active periods comprising:
   (a) saddle means mountable on a horse for supporting a rider;
   (b) girth means operably attachable to said saddle means for securing said saddle means to a horse;
   (c) electrode means operably mounted on said girth means for providing touching electrical contact means for providing touching electrical contact with the body of a horse mounted with said saddle means for detecting voltage changes on the skin surface of the horse and providing an electrical signal in response thereto;
   (d) signal processing circuitry means for processing said electrical signal from said electrode means;
   (e) display means for receiving said processed signal and generating a human readable display indicating the heart rate of a horse mounted with said saddle means; and
   (f) power supply means for providing electrical energy to operate said signal processing circuitry means and said display means.

2. The invention of claim 1 further comprising electrical connection means operably connectable between said electrode means and said signal processing circuitry means for transmitting said electrical signal from said electrode means to said signal processing circuitry means.

3. The invention of claim 2 wherein said signal processing circuitry means, said display means, and said power supply means are mounted within a housing means for protecting said signal processing circuitry means, said display means, and said power supply means.

4. The invention of claim 3 wherein said housing means is operably mounted on said saddle means on a forward portion thereof whereby said display means is readily readable by a person seated in said saddle means.

5. The invention of claim 4 wherein said housing means comprises socket means for receiving a terminal end portion of said electrical connection means in selectively engageable and disengageable relationship therewith.

6. The invention of claim 5 wherein said housing means comprises switching means for selectively switching said heart rate monitor on and off operably connected with said power supply means.

7. The invention of claim 6 wherein said display means comprises a liquid crystal display device.

8. The invention of claim 7 wherein said housing means is mounted on a pommel portion of said saddle means.

9. The invention of claim 8 wherein said housing means comprises a metallic box portion and an outer leather portion enclosing a substantial portion of said metallic box portion.

10. The invention of claim 2 wherein said electrode means comprises a first electrode, a second electrode and a third electrode mounted in spaced apart relationship along the length of said girth.

11. The invention of claim 10 wherein each said electrode is mounted in electrically isolated relationship with said girth.

12. The invention of claim 11 wherein each said electrode has an electrical lead wire associated therewith.

13. The invention of claim 12 wherein each said associated lead has an associated shielding means provided in encompassing relationship therewith for shielding signals transmitted from said electrodes to said signal processing circuitry means from outside noise signals.

14. The invention of claim 13 wherein said electrical connection means comprises said leads associated with said electrodes, said shielding means for said leads, and external casing means for physically protecting said leads and said shielding means.

15. The invention of claim 7 wherein said electrode means comprises a first electrode, a second electrode, and a third electrode mounted in spaced apart relationship along the length of said girth.

16. The invention of claim 15 wherein each said electrode is mounted in electrically isolated relationship with said girth.

17. The invention of claim 16 wherein each said electrode has an electrical lead associated therewith.

18. The invention of claim 17 wherein each said associated lead has an associated shielding means provided in encompassing relationship therewith for shielding signals transmitted from said electrodes to said signal processing circuitry means from outside noise signals.

19. The invention of claim 18 wherein said electrical connection means comprises said leads associated with said electrodes, said shielding means for said leads, and external casing means for physically protecting said leads and said shielding means.

20. The invention of claim 13 wherein each said electrode is provided with electrically conductive salve means for ensuring electrical contact between each said electrode and the body of a horse being monitored.

* * * * *